United States Patent [19]

Kadam et al.

[11] Patent Number: 5,284,947
[45] Date of Patent: Feb. 8, 1994

[54] MULTIPLE DRUG RESISTANCE-ATTENUATING COMPOUNDS

[75] Inventors: Sunil K. Kadam, Kenosha, Wis.; Patrick E. Humphrey, Lindenhurst, Ill.; Jill Hochlowski, Green Oaks, Ill.; James B. McAlpine, Libertyville, Ill.; Marianna Jackson, Waukegan, Ill.

[73] Assignee: Abbott Laboratories, Abbott Park, Ill.

[21] Appl. No.: 945,302

[22] Filed: Sep. 15, 1992

[51] Int. Cl.$^5$ .................. C07D 487/22; A61K 31/495
[52] U.S. Cl. ..................... 544/245; 435/119; 435/256.1
[58] Field of Search .......... 544/245; 514/250; 435/119, 254

[56] References Cited

U.S. PATENT DOCUMENTS

| | | | |
|---|---|---|---|
| 4,472,399 | 10/1981 | Kökösi et al. | 544/245 |
| 4,530,790 | 7/1985 | Monaghan et al. | 435/119 |
| 4,696,925 | 9/1987 | Houck et al. | 435/119 |
| 5,164,389 | 9/1991 | Chen | 514/250 |

OTHER PUBLICATIONS

Omura et al., The Journal of Antibiotics vol. XXXVIII No. 11, 1985; pp. 1631–1632.
Nooter et al., British Journal of Cancer, 63, 1991, pp. 663–669.
Liesch et al., The Journal of Antibiotics, vol. XXXVIII, No. 12, 1985; pp. 1638–1641.
III Rules Governing the Deposit Biological Maildrop.

*Primary Examiner*—Mukund J. Shah
*Assistant Examiner*—Pavanaram K. Sripada
*Attorney, Agent, or Firm*—Andreas M. Danckers

[57] ABSTRACT

A compound having the structural formula

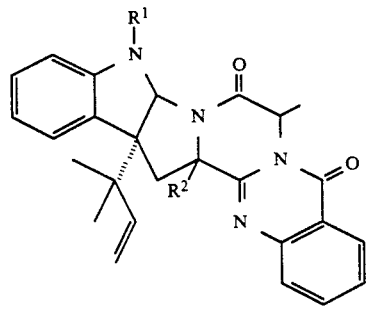

or a pharmaceutically acceptable salts and prodrugs thereof, wherein $R^1$ is selected from the group consisting of hydrogen and loweracyl, and $R^2$ is selected from the group consisting of hydrogen, hydroxyl and methoxyl, as well as methods for the preparation and use thereof.

10 Claims, 18 Drawing Sheets

$^1$H NMR Spectrum in CDCl$_3$ of 5-N-Acetylardeemin

13C CMR Spectrum in CDCl3 of 5-N-Acetylardeemin

Infrared Spectrum in CDCl₃ of 5-N-Acetylardeemin

1H NMR Spectrum in CDCl3 of Ardeemin

13C CMR Spectrum in CDCl3 of Ardeemin

Infrared Spectrum in CDCl3 of Ardeemin

1H NMR Spectrum in CDCl3 of 5-N-Acetyl-15b-β-hydroxyardeemin

13C CMR Spectrum in CDCl3 of 5-N-Acetyl-15b-β-hydroxyardeemin

Infrared Spectrum in CDCl3 of 5-N-Acetyl-15b-β-hydroxyardeemin

1H NMR Spectrum in CDCl3 of 15b-β-Hydroxyardeemin

13C CMR Spectrum in CDCl3 of 15b-β-Hydroxyardeemin

Infrared Spectrum in CDCl₃ of 15b-β-Hydroxyardeemin

1H NMR Spectrum in CDCl3 of 5-N-acetyl-15b-α-hydroxyardeemin

13C CMR Spectrum in CDCl3 of 5-N-acetyl-15b-α-hydroxyardeemin

Infrared Spectrum in $CDCl_3$ of 5-N-acetyl-15b-α-hydroxyardeemin

$^1$H NMR Spectrum in CDCl$_3$ of 15b-β-Methoxyardeemin

13C CMR Spectrum in CDCl3 of 15b-β-Methoxyardeemin

Infrared Spectrum in CDCl$_3$ of 15b-β-Methoxyardeemin

MULTIPLE DRUG RESISTANCE-ATTENUATING COMPOUNDS

TECHNICAL FIELD

The present invention relates to novel fused-ring compounds designated ardeemins and compositions thereof which are useful in the attenuation of multiple drug resistance, to processes for producing these compounds by fermentation of *Aspergillus fischeri*, and to a method of treating diseases in which multiple drug resistance is common by the administration of such compounds in combination with available cytotoxic drugs.

BACKGROUND OF THE INVENTION

Multiple drug resistance (MDR) is a well-known phenomenon wherein target cells, for example cancer cells, become resistant during treatment to different, structurally unrelated drugs in addition to the drug being used (Nooter et al., *Br. J. Cancer*, 63:663–669 (1991), incorporated herein by reference). Some compounds, such as verapamil, diltiazem, cyclosporin and catharanthine, are known to attenuate, if not reverse, drug resistance in certain mammalian target cells. While not intending to be limited by theory, it is believed that compounds affecting MDR interact with a membrane glycoprotein (P-170), a member of a superfamily of membrane transport proteins, which is the main component of membrane-associated drug efflux systems and is overexpressed in MDR cells. MDR resistance in other organisms, as for example resistance to the antimalarial drug chloroquine in *Plasmodium falciparum* and antimony resistance in Leishmania species, occurs by very similar mechanisms. Thus MDR-attenuating compounds have potential as adjuncts in antimalarial and other antiprotozoal as well as anticancer therapy.

Unfortunately, not all cells that develop MDR are responsive to known MDR attenuators. Moreover, some known MDR attenuators are active in vivo only at or near the toxic dose of these agents. There is therefore a continuing need for new compounds with MDR-attenuating activity.

The compounds of the present invention are related to but distinct from asperlicins, which are isolated from *Aspergillus alliaceus* and have activity as cholecystokinin antagonists (Leisch et al., *J. Antibiotics*, 38:1638–1641 (1985); Goetz et al., *J. Antibiotics*, 38:1631–1637 (1985); Houck et al., U.S. Pat. No. 4,696,925 (1987); Leish et al., *J. Antibiotics*, 41:878–881 (1988)).

SUMMARY OF THE INVENTION

In one aspect of the present invention are disclosed compounds having the general structural formula

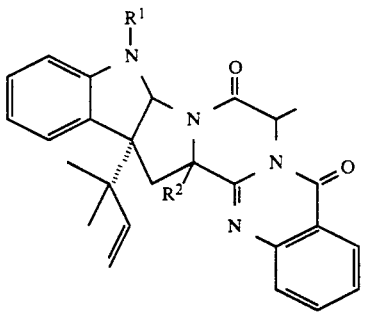

as well as the pharmaceutically acceptable salts and prodrugs thereof. In formula I, $R^1$ is hydrogen or lower-acyl, and $R^2$ is hydrogen, hydroxyl or methoxyl.

In a related aspect of the present invention are disclosed pharmaceutical compositions comprising a multiple drug resistance-attenuating amount of a compound of the invention in combination with a pharmaceutically acceptable carrier. Such compositions may additionally contain a therapeutically effective amount of a cytotoxic agent.

In a further aspect of the present invention, a process is disclosed for the preparation of the compounds of the invention, comprising (a) culturing of a suitable strain of *Aspergillus fischeri* in a medium containing assimilable sources of carbon and nitrogen and (b) isolating the compound from the medium. A strain of *Aspergillus fischeri* useful in the process of the invention is *Aspergillus fischeri* var. *brasiliensis*, strain AB 1826M-35, isolated in substantially pure culture and deposited under accession number NRRL 18896.

In another aspect of the present invention is disclosed a method of sensitizing a multiple drug resistant cell to a cytotoxic compound, comprising exposing said cell to a compound of the invention. Also disclosed is a method of treating a disease in which multiple drug resistance is common, comprising administering to a patient having such a disease a pharmaceutical composition of the invention which contains an inventive compound alone or in combination with an available cytotoxic agent.

BRIEF DESCRIPTION OF THE DRAWINGS

The present invention is described in connection with the appended drawings, in which.

DETAILED DISCLOSURE OF THE INVENTION

Figure 1:
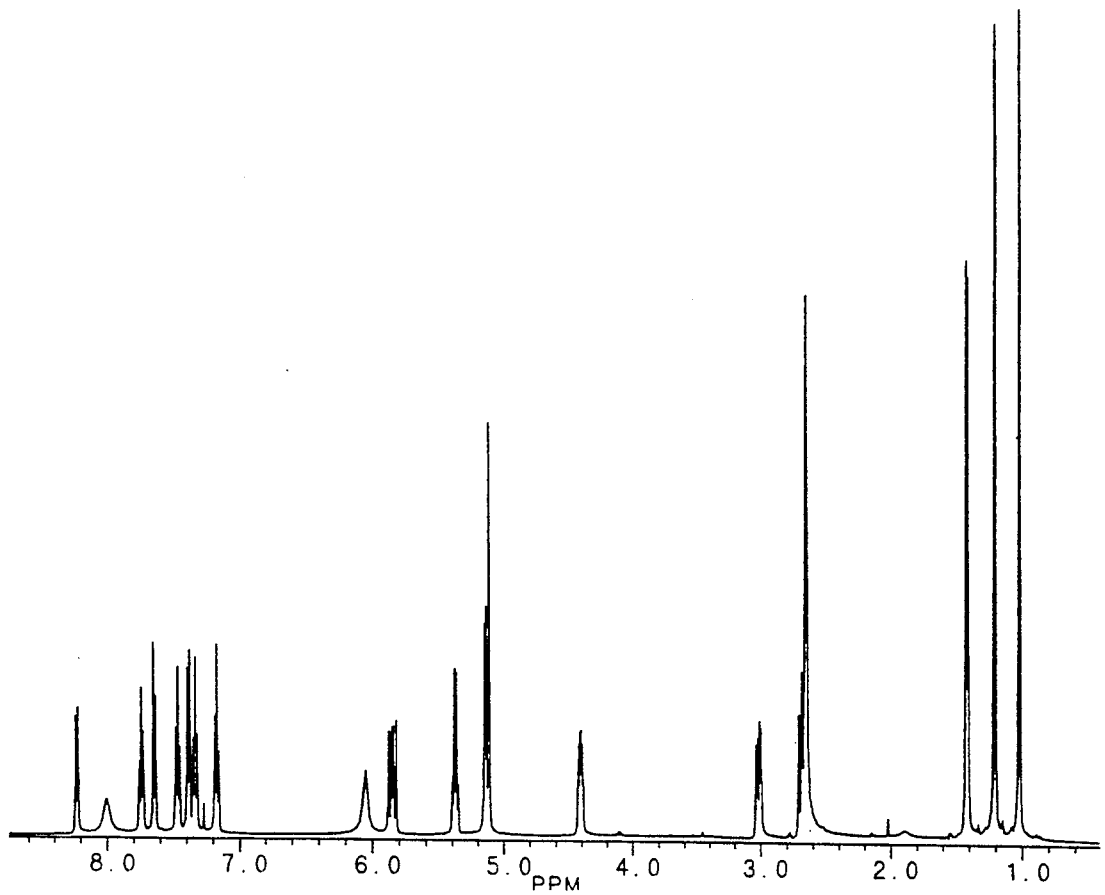
FIG. 1 is an $^1$H NMR spectrum in CDCl$_3$ of 5-N-acetylardeemin.

The compounds of the present invention, which are produced by the organism *Aspergillus fischeri*, have been given the generic name "ardeemins". The structural formula and numbering system of the principal ardeemin compound is as follows:

This compound and N-5 and C-15b derivatives thereof are found to have biological activity in the reversal of the effects of multiple drug resistance. Consequently, it is expected that these compounds may be used, in combination with known cytotoxic drugs, in the treatment of diseases in which the development of multiple drug resistance is common.

In particular, the compounds of the present invention are those of the above structural formula I or pharmaceutically-acceptable salts or prodrugs thereof, wherein R$^1$ is selected from the group consisting of hydrogen and loweracyl, and R$^2$ is selected from the group consisting of hydrogen, hydroxyl and methoxyl. Preferred compounds of the invention are those wherein R$^1$ is loweracyl and/or wherein R$^2$ is hydroxyl. Especially preferred compounds of the invention are those wherein R$^1$ is acetyl and R$^2$ is hydroxyl.

The following compounds are representative of the compounds of the present invention:
ardeemin;
5-N-acetylardeemin;
15b-$\beta$-hydroxy-5-N-acetylardeemin;
15b-$\beta$-hydroxyardeemin;
15b-$\alpha$-hydroxy-5-N-acetylardeemin; and
15b-$\beta$-methoxyardeemin.

As used herein, "loweralkyl" refers to a monovalent radical of from 1 to 6 carbon atoms derived from a straight- or branched-chain saturated hydrocarbon by the removal of a single hydrogen atom, as for example methyl, ethyl, n- and iso-propyl, and n-, sec-, iso- and tert-butyl.

"Loweracyl" represents a loweralkyl radical, as defined above, attached to the parent molecular moiety through a carbonyl group, as for example acetyl, propionyl and butanoyl.

"Prodrug" refers to compounds that are rapidly transformed in vivo to yield the parent compounds of the formula I, as for example by hydrolysis in blood. T. Higuchi and V. Stella provide a thorough discussion of the prodrug concept in "Prodrugs as Novel Delivery Systems", Vol. 14 of the A.C.S. Symposium Series, American Chemical Society (1975). Examples of esters useful as prodrugs for compounds containing carboxyl groups can be found on pages 14-21 of "Bioreversible Carriers in Drug Design: Theory and Application," edited by E. B. Roche, Pergamon Press (1987). Each of these references is incorporated by reference into the present application.

By a "therapeutically effective amount" of a compound of the invention is meant a sufficient amount of the compound to attenuate multiple drug resistance, at a reasonable benefit/risk ratio applicable to any medical treatment. It will be understood, however, that the total daily usage of the compounds and compositions of the present invention is to be decided by the attending physician within the scope of sound medical judgement. The specific therapeutically effective dose level for any particular patient will depend upon a variety of factors including the disorder being treated and the severity thereof; activity of the specific compound employed; the specific composition employed; the age, body weight, general health, sex and diet of the patient; the time of administration, route of administration, and rate of excretion of the specific compound employed; the duration of the treatment; drugs used in combination or coincidental with the specific compound employed; and like factors well known in the medical arts.

The total daily dose of the compounds of this invention administered to a human or other mammal in single or in divided doses can be in amounts of, for example, from about 0.01 to about 50 mg/kg body weight, or more usually from about 0.2 to about 30 mg/kg body weight. Single dose compositions may contain such amounts or submultiples thereof to make up the daily dose. In general, treatment regimens according to the present invention comprise administering to a patient in need of such treatment from about 20 mg to about 2000 mg of the compound(s) of this invention per day in multiple doses or in a single dose.

The compounds of this invention may be administered alone or in combination or in concurrent therapy with other agents. Liquid dosage forms for oral administration may include pharmaceutically acceptable emulsions, microemulsions, solutions, suspensions, syrups and elixirs containing inert diluents commonly used in the art such as water. Such compositions may also comprise adjuvants, such as wetting agents; emulsifying and suspending agents; and sweetening, flavoring and perfuming agents.

Injectable preparations, as for example sterile injectable aqueous or oleaginous suspensions, may be formulated according to the known art using suitable dispersing or wetting agents and suspending agents. The sterile injectable preparation may also be a sterile injectable solution, suspension or emulsion in a nontoxic parenterally acceptable diluent or solvent, such as a solution in 1,3-butanediol. Among the acceptable vehicles and solvents that may be employed are sterile, fixed oils which are conventionally employed as a solvent or suspending medium, such as synthetic mono- or diglycerides, or fatty acids such as oleic acid.

The injectable formulation can be sterilized, as for example by filtration through a bacteria-retaining filter, or by incorporating sterilizing agents in the form of sterile solid compositions which can be dissolved or dispersed in the injectable medium just prior to use.

In order to prolong the effect of a drug, it is often desirable to slow the absorption of a drug by subcutaneous or intramuscular injection. The most common way to accomplish this is to inject a suspension of crystalline or amorphous material with poor water solubility. The rate of absorption of the drug becomes dependent on the rate of dissolution of the drug which is, in turn, dependent on the physical state of the drug, for example, the crystal size and the crystalline form. Another approach to delaying absorption of a drug is to administer the drug as a solution or suspension in oil. Injectable depot forms can also be made by forming microcapsule matrices of drugs and biodegradable polymers such as polylactide-polyglycolide. Depending on the ratio of drug to polymer and the composition of the polymer, the rate of drug release can be controlled. Examples of other biodegradable polymers include poly-orthoesters and polyanhydrides. The depot injectables can also be made by entrapping the drug in liposomes or microemulsions which are compatible with body tissues.

Suppositories for rectal administration of the drug can be prepared by mixing the drug with a suitable nonirritating excipient such as cocoa butter and polyethylene glycol which are solid at room temperature but liquid at body temperature and will therefore melt in the rectum and release the drug.

Solid dosage forms for oral administration may include capsules, tablets, pills, powders, prills and granules. In such solid dosage forms the active compound may be admixed with at least one inert diluent such as sucrose, lactose or starch. Such dosage forms may also comprise, as is normal practice, additional substances other than inert diluents such as tableting lubricants and other tableting aids such as magnesium stearate and microcrystalline cellulose. In the case of capsules, tablets and pills, the dosage forms may also comprise buffering agents. Tablets and pills can additionally be prepared with enteric coatings and other release-controlling coatings.

Solid compositions of a similar type may also be employed as fillers in soft and hard-filled gelatin capsules using such excipients as lactose or milk sugar as well as high molecular weight polyethylene glycols and the like.

The active compounds can also be in micro-encapsulated form with one or more excipients as noted above. The solid dosage forms of tablets, dragees, capsules, pills, and granules can be prepared with coatings and shells such as enteric coatings and other coatings well known in the pharmaceutical formulating art. They may optionally contain opacifying agents and can also be of a composition that they release the active ingredient(s) only, or preferably, in a certain part of the intestinal tract, optionally in a delayed manner. Examples of embedding compositions which can be used include polymeric substances and waxes.

Dosage forms for topical or transdermal administration of a compound of this invention include ointments, pastes, creams, lotions, gels, powders, solutions, sprays, inhalants or patches. The active component is admixed under sterile conditions with a pharmaceutically acceptable carrier and any needed preservatives or buffers as may be required. Ophthalmic formulations, ear drops, eye ointments, powders and solutions are also contemplated as being within the scope of this invention.

The ointments, pastes, creams and gels may contain, in addition to an active compound of this invention, excipients such as animal and vegetable fats, oils, waxes, paraffins, starch, tragacanth, cellulose derivatives, polyethylene glycols, silicones, bentonites, silicic acid, talc and zinc oxide, or mixtures thereof.

Powders and sprays can contain, in addition to the compounds of this invention, excipients such as lactose, talc, silicic acid, aluminum hydroxide, calcium silicates and polyamide powder, or mixtures of these substances. Sprays can additionally contain customary propellants such as chlorofluorohydrocarbons or suitable alternatives.

Transdermal patches have the added advantage of providing controlled delivery of a compound to the body. Such dosage forms can be made by dissolving or dispersing the compound in the proper medium. Absorption enhancers can also be used to increase the flux of the compound across the skin. The rate can be controlled by either providing a rate controlling membrane or by dispersing the compound in a polymer matrix or gel.

The compounds of the present invention may be produced by culturing microorganisms belonging to the genus Aspergillus which are capable of producing compounds of Formula I in appropriate media. Although other culture methods are feasible, a liquid, submerged, agitated culture process is preferred. The culture is grown in a culture medium which includes a source of carbon and a source of nitrogen. Media which are useful include an assimilable source of carbon, such as starch, sugar, molasses, glycerol, or a combination of glucose plus molasses; an assimilable source of nitrogen, such as protein, protein hydrolysate, polypeptides, amino acids, or peptone plus yeast extract or whole yeast; and other organic and inorganic ingredients which can be added to stimulate production of the compounds of Formula I. For example, inorganic anions and cations, including potassium, magnesium, calcium, ammonium, sulfate, carbonate, phosphate and chloride may be added. Buffers, such as calcium carbonate, may also be added to aid in controlling the pH of the fermentation medium.

Aeration can be provided by forcing sterile air through the fermentation medium. Agitation can be provided by shaking the container or by stirring the culture, for example, with a mechanical stirrer.

The fermentation is generally carried out in a temperature range of from about 20° C. to about 35° C., with the pH of the fermentation medium preferably being maintained between 3 and 9. The compounds are produced and accumulated between 3 and 14 days after inoculation of the fermentation.

To isolate the compounds of the invention, the fermentation broth is removed from the fermentor and diluted with a suitable water-miscible solvent, as for example acetone, methanol, ethanol or isopropanol. The resultant mixture is then extracted with a water-immiscible organic solvent such as chloroform, methylene chloride or ethyl acetate. The organic extract is combined and concentrated to a suspension. This suspension is partitioned between a suitable two phase, aqueous solvent system, as for example equal volumes of chloroform, methanol and distilled water. The lower layer from this partition is concentrated to dryness and chromatographed over a column of size-exclusion resin such as SEPHADEX LH-20, eluting with a suitable solvent such as methanol. The active material from this column is subjected to repeated countercurrent chromatography on a suitable instrument such as an Ito multi-layered coil planet centrifuge or other countercurrent chromatographic apparatus, utilizing several different two phase solvent systems, as for example hexane-ethyl acetate-methanol-water in various ratios. The separate fractions are combined as appropriate, the solvents are removed under vacuum, and the products are dryed.

The foregoing will be better understood by reference to the following examples, which are provided for purposes of illustration and are not intended as a limitation upon the scope of the invention.

EXAMPLE 1

Characterization of the microorganism

The microorganism producing the compounds of the invention was a novel variant of the fungus *Aspergillus fischeri*, named *Aspergillus fischeri* var. *brasiliensis*, strain AB 1826M-35. The culture was deposited with the National Center for Agricultural Utilization Research, Peoria, Ill., and assigned the accession number NRRL 18896. *A. fischeri* var. *brasiliensis* NRRL 18896 was isolated from a soil sample obtained in Brazil. The morphological and cultural characteristics of the strain on three media are described below. The culture was incubated for fourteen days at 24° C. and 37° C. Descriptions are correct for both temperatures unless otherwise stated. The color and number in parenthesis were assigned based on the Inter-Society Color Council-National Bureau of Standards (ISCC-NBS) Centroid Color Charts, U.S. Dept. of Commerce supplement to NBS Cir. 553, Washington, D.C., 1976.

Growth on Czapek Dox agar

Colonies of strain AB 1826M-35 on Czapek Dox agar were cottony, white (263), produced a clear exudate and grew rapidly to 13-15 cm in diameter. The reverse was pale yellow pink (31). Cleistothecia were absent on media prepared with 3 and 30 percent sucrose but were moderately produced on a 0.3 percent sucrose medium. Conidiophores were absent on 0.3 and 3 percent sucrose media but moderate formation occurred with 30 percent sucrose and were more numerous at colony margins. The conidiophores measured 30-160 $\mu m \times 7$-10 $\mu m$. Vesicles were 10-12 $\mu m$ in diameter, flask shaped, smooth to delicately roughened and colorless. Conidial heads were 30-400 $\mu m \times 15$-25 $\mu m$, columnar but diverging somewhat near the terminus. Phialides were uniseriate, crowded and bottle-shaped and fertile over the upper half of the conidial head. The conidia were smooth to slightly roughened, globose to subglobose in shades of grayish green (150) to light grayish olive (109) with age and were 1.4-1.7 $\mu m \times 1.7$-2.0 $\mu m$ in diameter.

Growth on Blakeslee's malt extract agar

On Blakeslee's malt extract agar, colonies grew rapidly to 13-15 cm in diameter. The aerial mycelium was felted, and the colony formed a tough basal mycelium. The colonies were yellowish white (92) with a continuous layer of cleistothecia. The reverse was pale greenish yellow (104) with no exudate. Conidiophore formation was sparse at 24° C. and did not influence colony appearance. Conidiophores were more abundant at 37° C., measuring 50-200 $\mu m \times 2.5$-3.25 $\mu m$. The phialides were 1.8-2.1 $\mu m \times 4$-6 $\mu m$. Cleistothecia were produced within a cottony mass of mycelium. At 24° C., they were yellowish white (92), globose to subglobose and 250-500 $\mu m$ in diameter; walls were thin and delicate, consisting of flattened mycelial cells. At 37° C., cleistothecia were smaller (50-175 $\mu m$ in diameter), globose or nearly so, delicate and were colored white (263) to yellowish white (92). Asci were 8-12 $\mu m$ in diameter and contained eight spores. Ascospores were uncolored and nearly globose. The spore bodies were 4.5-5 $\mu m$ in diameter with two flexuous equatorial bands about 1 $\mu m$ apart. In face view, bands were 6-8 sided polygons. The convex surfaces of the spores were covered by spiny projections less than 0.5 $\mu m$ in length. Structures were generally larger on malt extract than on Czapek Dox or potato dextrose agars.

Growth on potato dextrose agar

On potato dextrose agar colonies grew rapidly to 13-15 cm in diameter. They were white (263) with felted mycelia and produced a clear, pale yellow (89) exudate. The reverse was dark reddish gray (23) at the colony center to light grayish brown (60) at the margins. Cleistothecia were white (263) to yellowish white (92). Cleistothecia formation was moderate, and they ranged in size from 150 to 500 $\mu m$ in diameter at 24° C. but were smaller and more abundant at 37° C. Conidiophore production was very limited and were found primarily at colony margins. They measured 40-250 $\mu m \times 2$-4 $\mu m$. Phialides were 2 $\mu m \times 4$-6 $\mu m$.

The properties of strain AB 1826M-35 were compared to those reported by Raper and Fennel in "The Genus Aspergillus", Baltimore, 1965. This study indicated that AB 1826M-35 closely resembled *A. fischeri* and *A. fischeri* var. *spinosus*. A laboratory comparison of strain AB 1826M-35 with the type strains *A. fischeri* Wehmer ATCC 1020 and *A. fischeri* var. *spinosus*. ATCC 16898 showed that the strain of the present invention, although similar, differed from the other two in a number of morphological characteristics. These differences warrant the designation of culture AB 1826M-35 as the variant *Aspergillus fischeri* var. *brasiliensis*.

EXAMPLE 2

Fermentation process

*Aspergillus fischeri* AB 1826M-35 (NRRL 18896) was maintained as a frozen inoculum stock by freezing a portion of the original inoculum and storing it at −70° C. The medium described in Table 1 was used for seed growth and the medium described in Table 2 was used for production.

The media were prepared for seeding as follows: Six hundred mL of the seed medium (Table 1) were dispensed into 2 liter Erlenmeyer flasks. The flasks were sterilized for 35 minutes at 121° C., 15 psi. To cooled medium in seed flasks was added 2.5 mL of frozen inoculum. The seed flasks were incubated for 72 hours at 28° C. on a rotary shaker with a stroke of 2 inches, operated at 225 rpm.

Thirty liters of production medium (Table 2) were prepared in a 42-liter stainless steel stirred fermentor (LH Fermentation). Lactose and glucose monohydrate were sterilized separately and added to the fermentor after sterilization. The remaining ingredients of the production medium were sterilized in the fermentor at 121° C. and 15 psi for 1 hour. Antifoam agent XFO-371 (Ivanhoe Chemical Co., Mundelein, Ill.) was added initially at 0.01%, and then as required. The fermentor was inoculated with 1.5 liters of the seed flask growth. The temperature was controlled at 22° C. The agitation rate was 250 rpm and the air flow was 0.7 vol/vol/min. The head pressure was maintained at 5 psi. The fermentation was terminated at nine days, with a harvest volume of 29 liters.

TABLE 1

| Ingredients | grams/Liter |
| --- | --- |
| Seed medium | |
| Corn steep powder | 2.5 |
| (Roquette Corp., Gurnee, IL) | |
| Glucose monohydrate | 10.0 |
| Oat flour | 10.0 |
| (National Oats Co., Cedar Rapids, IA) | |
| Tomato paste | 40.0 |
| (Contadina Foods, Inc., Los Angeles, CA) | |
| $CaCl_2.2H_2O$ | 10.0 |
| Trace element solution | 10 ml/L |
| Distilled water was added to achieve a volume 1 liter. | |
| The pH was adjusted to pH 6.8 with 10N NaOH. | |
| Trace element solution | |
| $FeSO_4.7H_2O$ | 1.0 |
| $MnCl_2.4H_2O$ | 1.0 |
| $CuCl_2.2H_2O$ | 0.025 |
| $CaCl_2.2H_2O$ | 0.1 |
| $H_3BO_3$ | 0.56 |
| $(NH_4)_6MoO_2.4H_2O$ | 0.019 |
| $ZnSO_4.7H_2O$ | 0.2 |
| Distilled water was added to achieve a volume of 1 liter. | |

TABLE 2

| Production medium | |
| --- | --- |
| Ingredient | grams/Liter |
| Lactose* | 30.0 |
| Glucose monohydrate* | 20.0 |
| Ammonium acetate | 5.0 |
| Sodium acetate | 4.1 |
| $KH_2PO_4$ | 2.0 |
| $FeSO_4.7H_2O$ | 0.2 |
| $CuSO_4.5H_2O$ | 0.005 |
| $ZnSO_4.7H_2O$ | 0.02 |
| Distilled water was added to 1 liter. | |
| The pH was adjusted to 6.2 with 10N sulfuric acid. | |

*Lactose and glucose monohydrate were sterilized separately.

EXAMPLE 3

Isolation of the compounds of Formula 1

To 20L of fermentation broth from Example 2 were added 8L of acetone and the mixture was stirred for 3 hours. To this mixture was added 16L of ethyl acetate with additional stirring for 1 hour. The ethyl acetate layer was removed, and an additional 16L of ethyl acetate added to the aqueous acetone mixture and stirred for 1 hour. The second ethyl acetate layer was removed and combined with the first extract and concentrated. The resulting aqueous suspension was partitioned between equal volumes of distilled water-chloroform-methanol (1.5L of each). The upper layer from this partition was extracted twice with 0.7L of chloroform, and the lower layers were combined and concentrated to give an oil. This oil was chromatographed over a SEPHADEX LH-20 resin column (8 cm diam., 80 cm length) eluted with methanol. Active fractions from this column were combined and concentrated to an oil. This oil was subjected to countercurrent chromatography on an Ito multi-layered coil planet centrifuge in a solvent system of hexane-ethyl acetate-methanol-distilled water (1:1:1:1) with the upper phase stationary. Active fractions, identified by bioassay, where further examined for homogeneity by thin layer chromotography (TLC) and were combined to yield pure compounds 1 (67 mg), 3 (56 mg) and 4 (1 mg), as well as mixed component fractions designated as Pool A and Pool B.

Pool A was subjected to countercurrent chromatography on an Ito multi-layered coil planet centrifuge in a solvent system of hexane-ethyl acetate-methanol-distilled water (2:3:3:2) with the lower phase stationary. Active fractions from this chromatography were combined and subjected to countercurrent chromatography in a solvent system of hexane-methylene chloride-methanol-distilled water (5:1:1:1) with the lower phase stationary. Active fractions were combined based upon their TLC behavior to yield pure compounds 3 (40 mg) and 5 (4 mg).

Pool B was subjected to countercurrent chromatography in a solvent system of hexane-methylene chloride-methanol-distilled water (5:1:1:1) with the lower phase stationary. Active fractions from this chromatography were combined and concentrated to an oil. This oil was subjected to further countercurrent chromatography in a solvent system of hexane-ethyl acetate-methanol-distilled water (70:30:15:6) with the upper phase stationary. Fractions were combined based upon their TLC behavior and concentrated to yield pure compounds 2 (8 mg) and 6 (12 mg).

EXAMPLE 4

5-N-Acetylardeemin (Formula I: $R^1 = -C(O)CH_3, R^2 =$ hydrogen)

Figure 2:
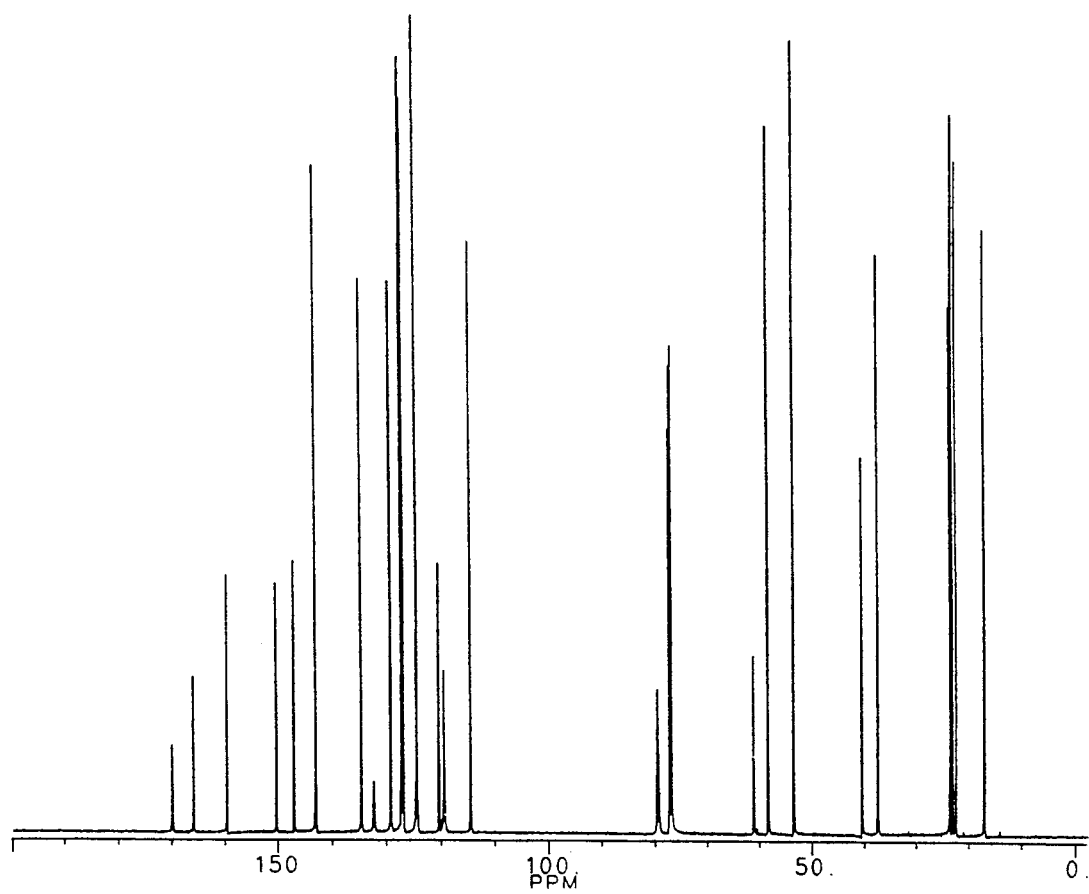
FIG. 2 is a $^{13}$C CMR spectrum in CDCl$_3$ of 5-N-acetylardeemin.
Figure 3:
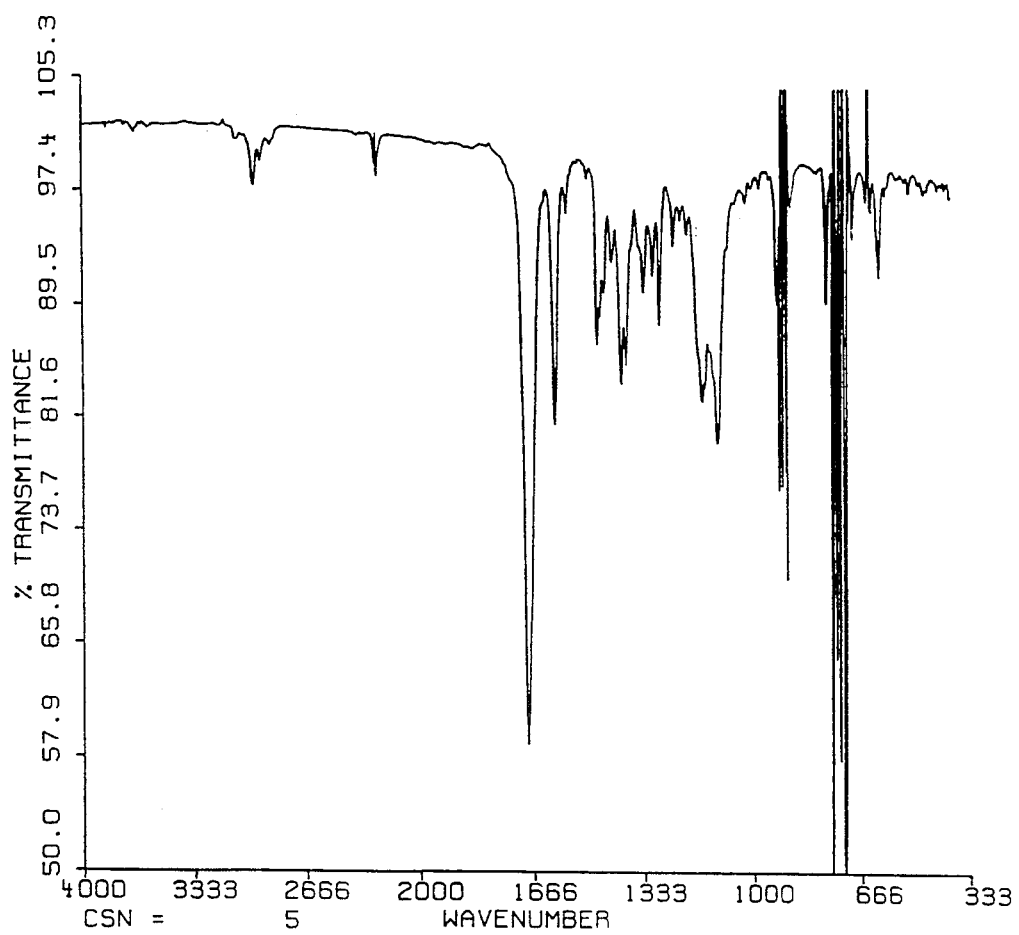
FIG. 3 is an infrared spectrum in CDCl$_3$ of 5-N-acetylardeemin.

5-N-Acetylardeemin, isolated as pure compound number 1 in Example 3 above, was found to be a white solid, mp 226°–228° C. $[\alpha]_D^{25} = -33°$ (c=0.78, MeOH). Thin layer chromatography (TLC) on Merck silica gel plates, with visualization by ultraviolet fluorescence quenching at 254 nm and by spraying with ceric sulfate reagent showed the compound to have the following Rf values: Rf=0.69 in EtOAc, Rf=0.56 in $CHCl_3$/MeOH (97/3), and Rf=0.56 in toluene/acetone (2/1). A chemical formula of $C_{28}H_{28}N_4O_3$ was established by high resolution electron impact mass spectroscopy (exact mass=468.2168, calc mass=468.2161). The ultraviolet spectrum (MeOH) contained bands at $\lambda_{max}=210$ ($\epsilon=10,700$), 224 ($\epsilon=10,700$), 264 ($\epsilon=4,300$), 274 ($\epsilon=4,000$), 302 ($\epsilon=1,700$), and 314 ($\epsilon=1,360$). These bands were unchanged with the addition of acid or base. $^1H$ NMR, $^{13}C$ NMR and IR spectra are provided below in FIGS. 1, 2 and 3, respectively.

EXAMPLE 5

Ardeemin (Formula I: $R^1 = R^2 =$ hydrogen)

Figure 4:
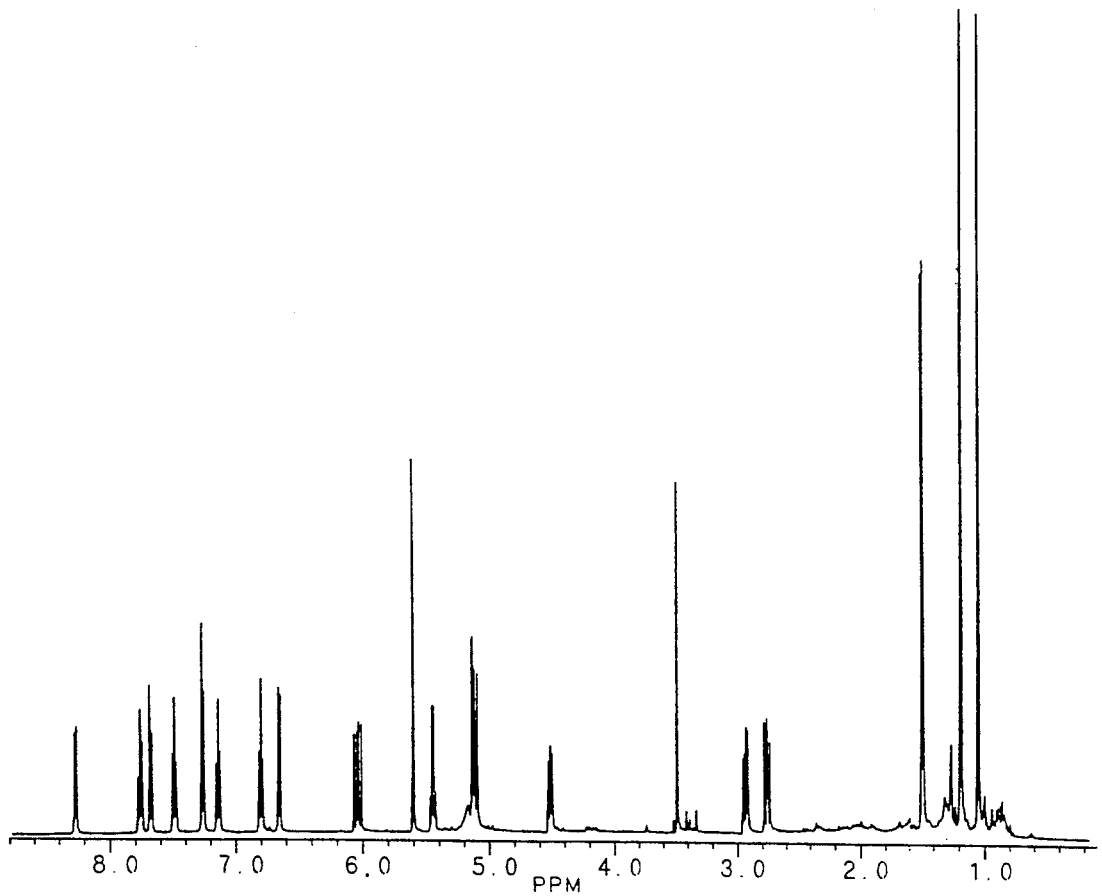
FIG. 4 is an $^1$H NMR spectrum in CDCl$_3$ of ardeemin.
Figure 5:
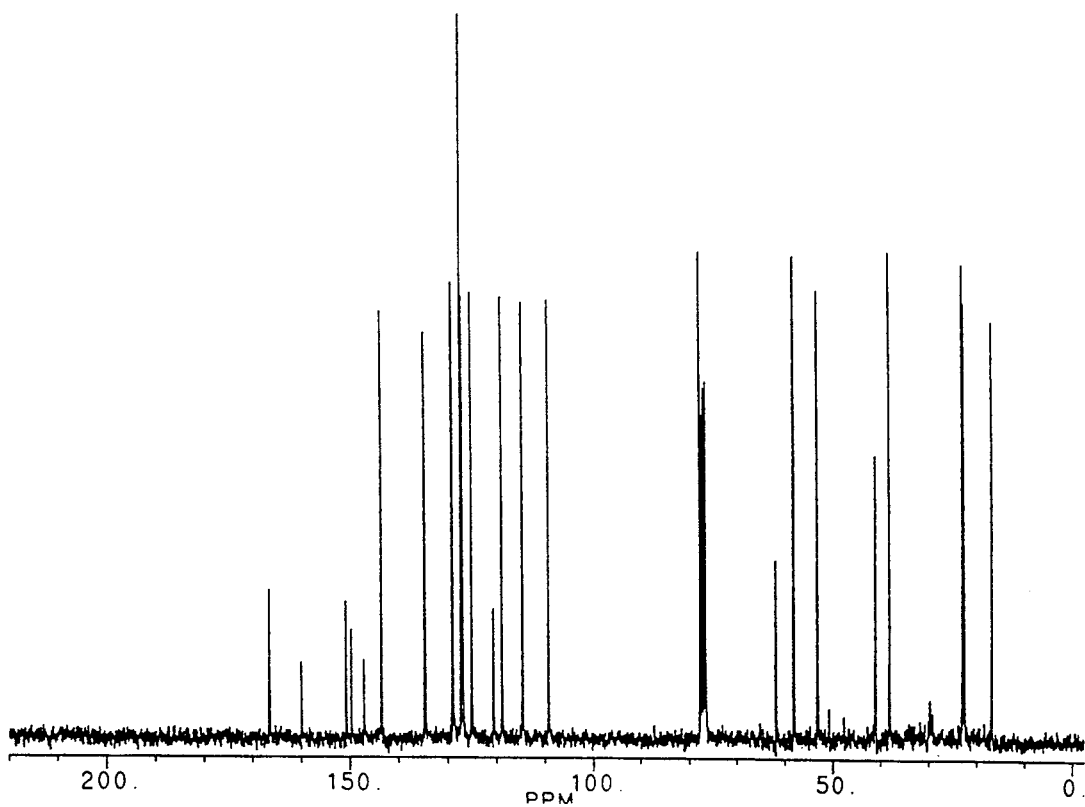
FIG. 5 is a $^{13}$C CMR spectrum in CDCl$_3$ of ardeemin.
Figure 6:
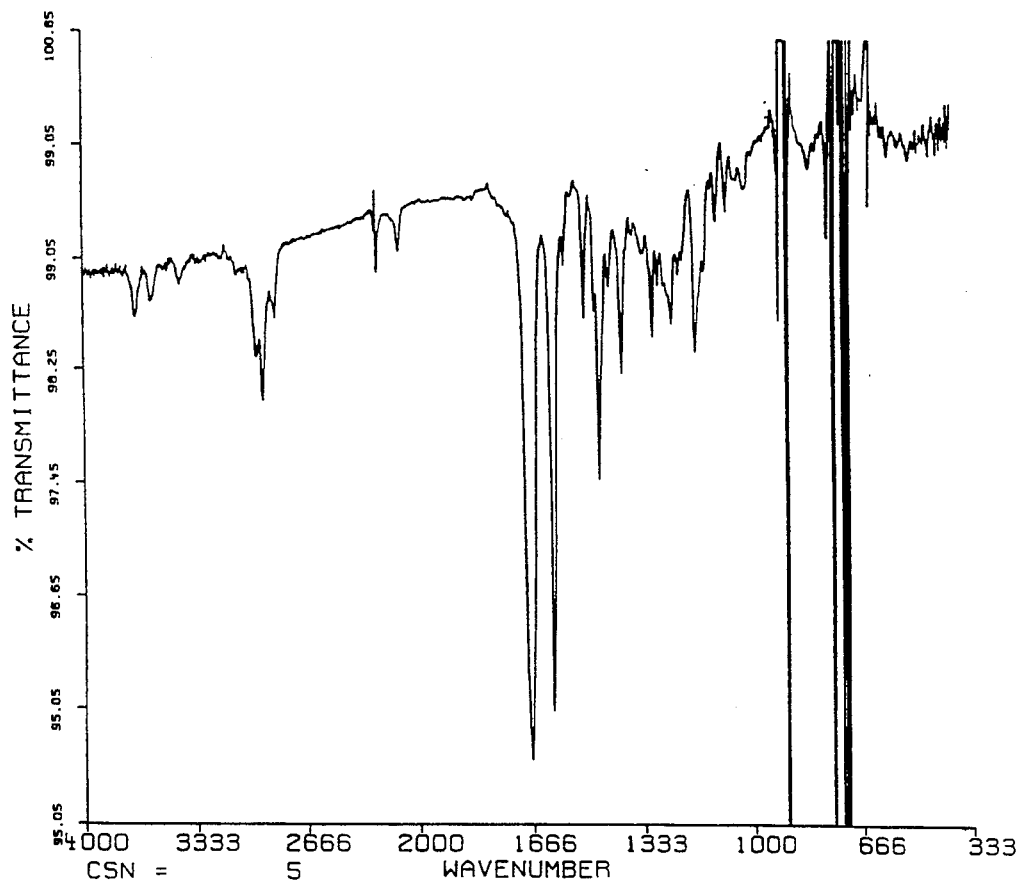
FIG. 6 is an infrared spectrum in CDCl$_3$ of ardeemin.

Ardeemin, isolated as pure compound number 2 in Example 3 above, was found to be a white solid, $[\alpha]_D^{25} = -92°$ (c=0.24, MeOH). TLC as described in Example 4 showed the compound to have the following Rf values: Rf=0.69 in EtOAc, Rf=0.56 in $CHCl_3$/MeOH (97/3) and Rf=0.56 in toluene/acetone (2/1). A molecular weight of 426 was established by desorption chemical ionization mass spectroscopy ($NH_3$ gas). The ultraviolet spectrum (MeOH) contained bands at $\lambda_{max}=210$ ($\epsilon=12,600$), 224 ($\epsilon=7,400$), 268 ($\epsilon=2,700$), 274 ($\epsilon=2,800$), 302 ($\epsilon=2,600$), and 314 ($\epsilon=2,000$). These bands were unchanged with the addition of acid or base. $^1H$ NMR, $^{13}C$ NMR, and IR spectra are provided below in FIGS. 4, 5 and 6, respectively.

EXAMPLE 6

5-N-Acetyl-15b-$\beta$-hydroxyardeemin (Formula I: $R^1 = -C(O)CH3$, $R^2 =$ hydroxyl)

Figure 7:
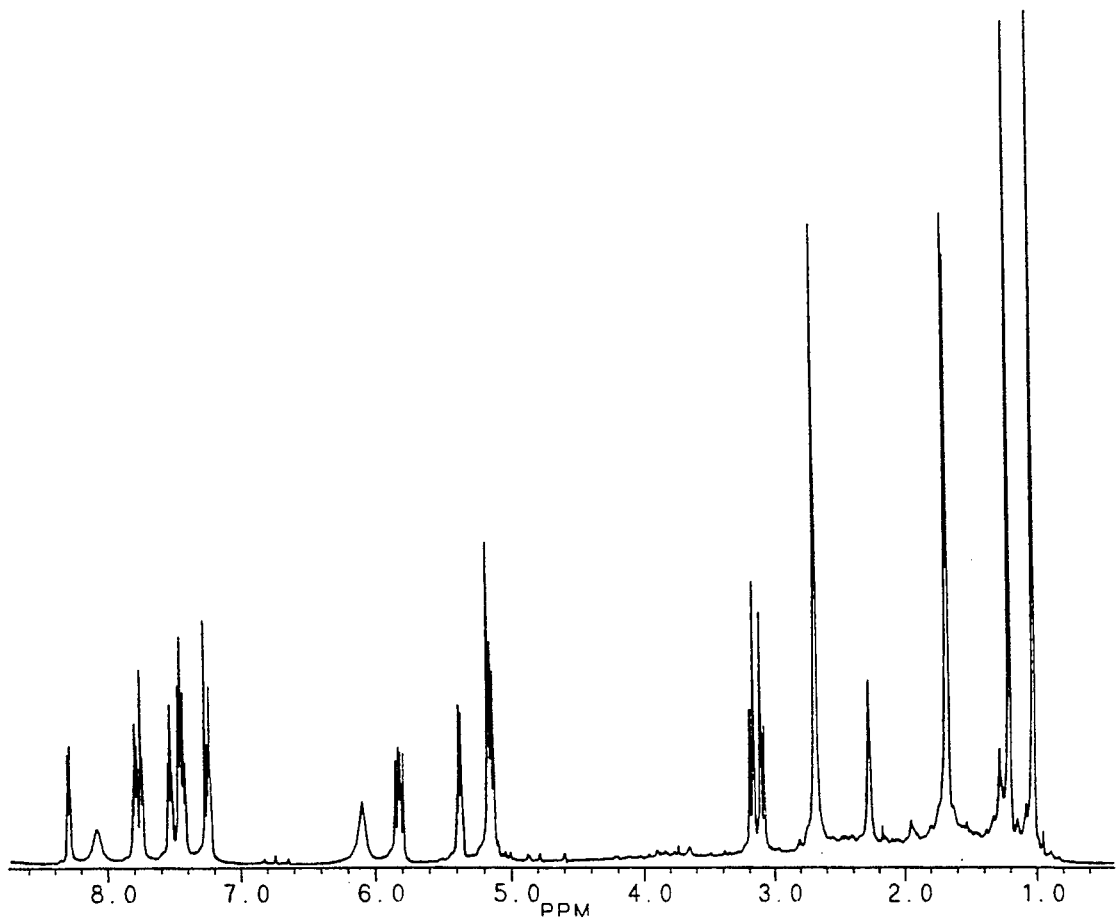
FIG. 7 is an $^1$H NMR spectrum in CDCl$_3$ of 5-N-acetyl-15b-$\beta$-hydroxyardeemin.
Figure 8:
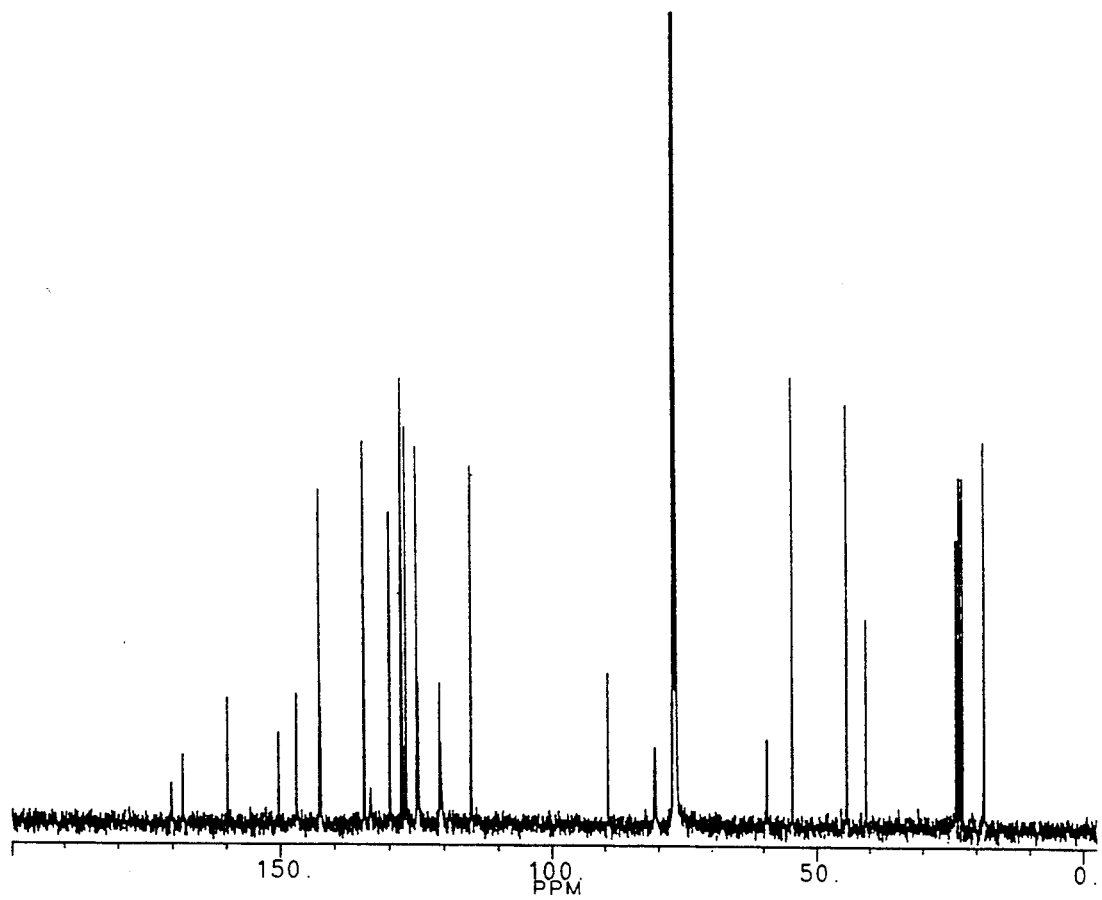
FIG. 8 is a $^{13}$C CMR spectrum in CDCl$_3$ of 5-N-acetyl-15b-$\beta$-hydroxyardeemin.
Figure 9:
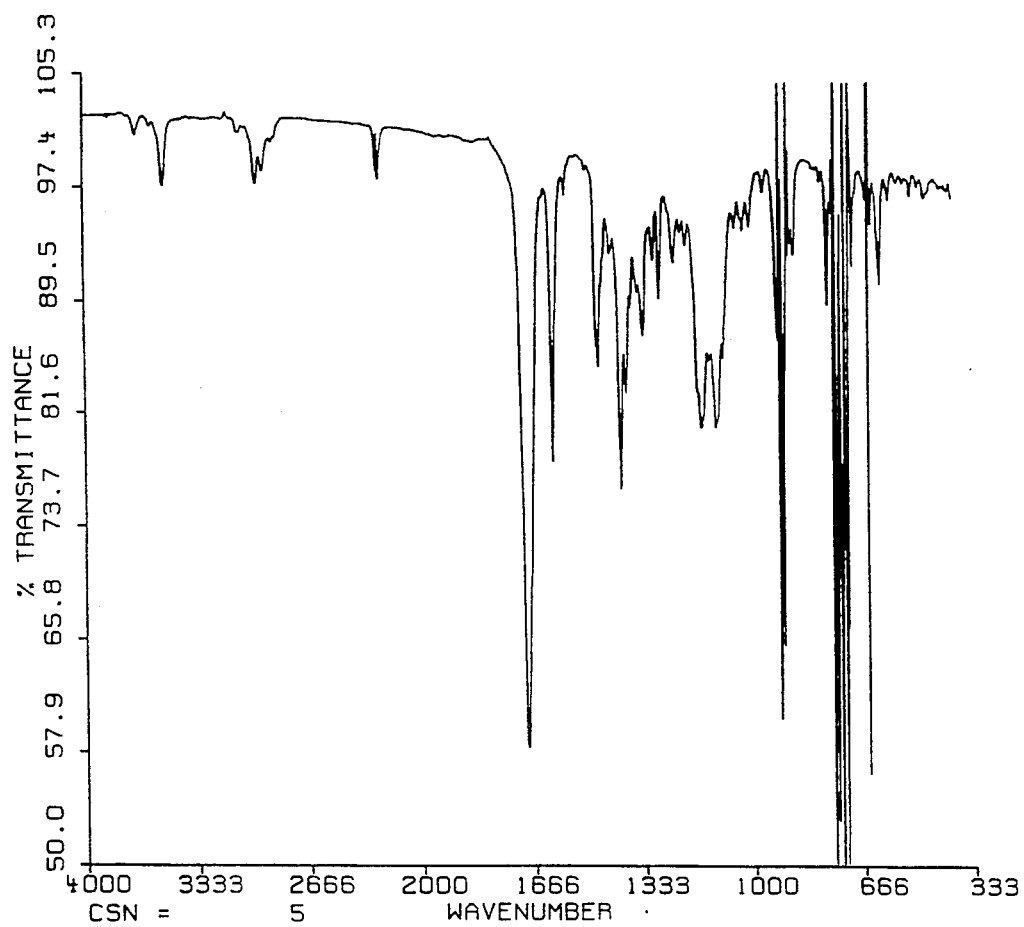
FIG. 9 is an infrared spectrum in CDCl$_3$ of 5-N-acetyl-15b-$\beta$-hydroxyardeemin.

5-N-Acetyl-15b-$\beta$-hydroxyardeemin, isolated as pure compound number 3 in Example 3 above, was found to be a white solid, $[\alpha]_D^{25} = -245°$ (c=0.21, MeOH). TLC as described in Example 4 showed the compound to have the following Rf values: Rf=0.64 in EtOAc, Rf=0.50 in CHCl$_3$/MeOH (97/3) and Rf=0.39 in toluene/acetone (2/1). A chemical formula of $C_{28}H_{28}O_4N_4$ was established by high resolution electron impact mass spectroscopy (exact mass=484.2118, calc mass=484.2110). An ultraviolet spectrum obtained in MeOH contained bands at $\lambda_{max}=210$ ($\epsilon=13,000$), 224 ($\epsilon=8,000$), 268 ($\epsilon=2,600$), 274 ($\epsilon=2,400$), 302 ($\epsilon=1,200$), and 314 ($\epsilon=1,200$). These bands were unchanged with the addition of acid or base. $^1$H NMR, $^{13}$C NMR, and IR spectra are provided below in FIGS. 7, 8 and 9, respectively.

EXAMPLE 7

15b-$\beta$-Hydroxyardeemin (Formula I: $R^1 =$ hydrogen, $R^2 =$ hydroxyl)

Figure 10:
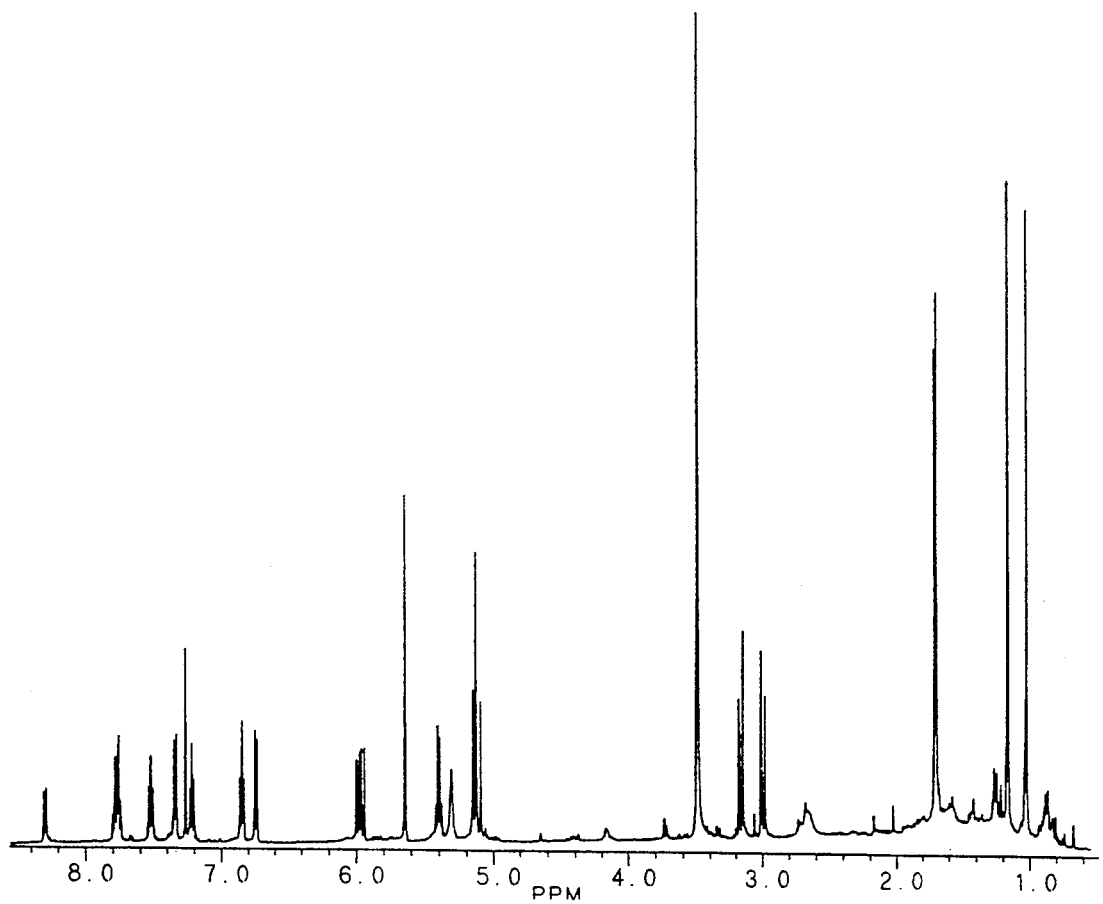
FIG. 10 is an $^1$H NMR spectrum in CDCl$_3$ of 15b-$\beta$-hydroxyardeemin.
Figure 11:
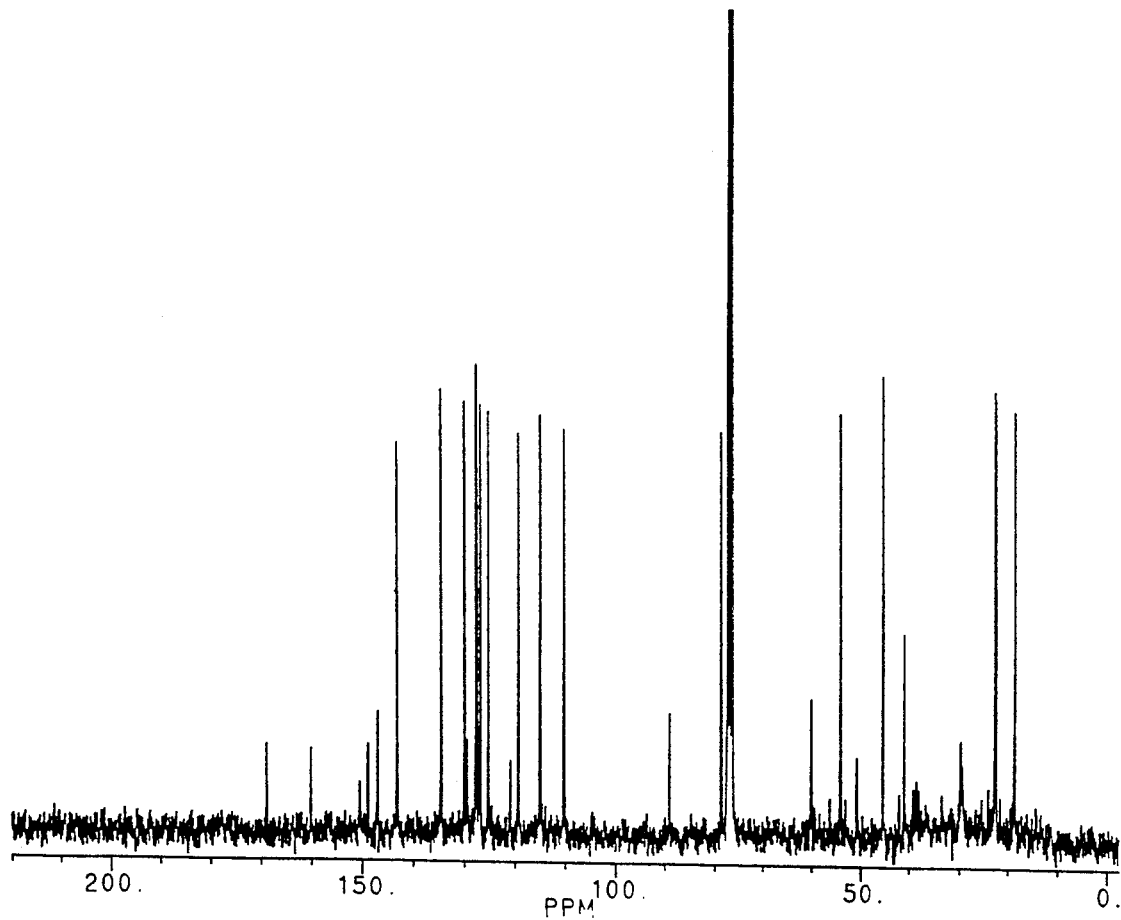
FIG. 11 is a $^{13}$C CMR spectrum in CDCl$_3$ of 15b-$\beta$-hydroxyardeemin.
Figure 12:
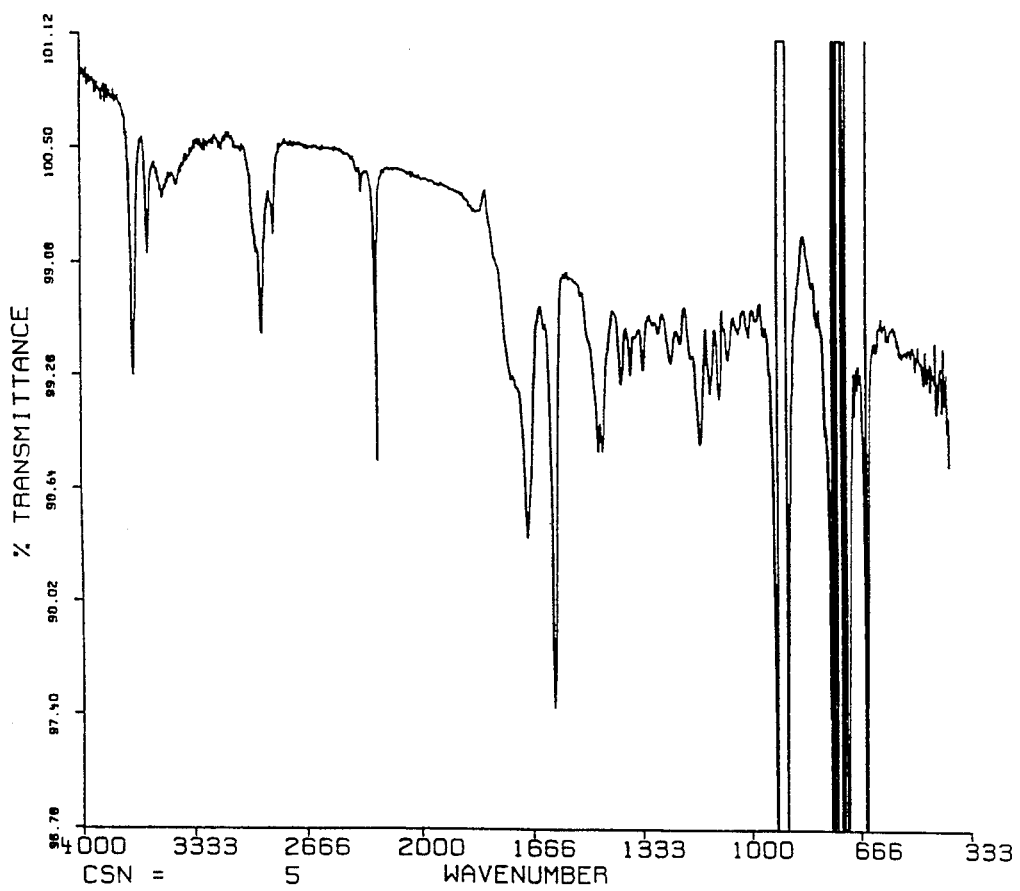
FIG. 12 is an infrared spectrum in CDCl$_3$ of 15b-$\beta$-hydroxyardeemin.

15b-$\beta$-Hydroxyardeemin, isolated as pure compound number 4 in Example 3 above, was found to be a white solid, $[\alpha]_D^{25} = -4°$ (c=0.08, MeOH). TLC as described in Example 4 showed the compound to have the following Rf values: Rf=0.69 in EtOAc, Rf=0.60 in CHCl$_3$/MeOH (97/3), and Rf=0.55 in toluene/acetone (2/1). A molecular weight of 442 was established by desorption chemical ionization mass spectroscopy (NH$_3$ gas). An ultraviolet spectrum (MeOH) contained bands at $\lambda_{max}=210$ ($\epsilon=3,500$), 224 ($\epsilon=1,900$), 268 ($\epsilon=800$), 274 ($\epsilon=800$), 302 ($\epsilon=600$), and 314 ($\epsilon=550$). These bands were unchanged with the addition of acid or base. $^1$H NMR $^{13}$C NMR, and IR spectra are provided below in FIGS. 10, 11 and 12, respectively.

EXAMPLE 8

5-N-Acetyl-15b-$\alpha$-hydroxyardeemin (Formula I: $R^1 = -C(O)CH3$, $R^2 =$ hydroxyl)

Figure 13:
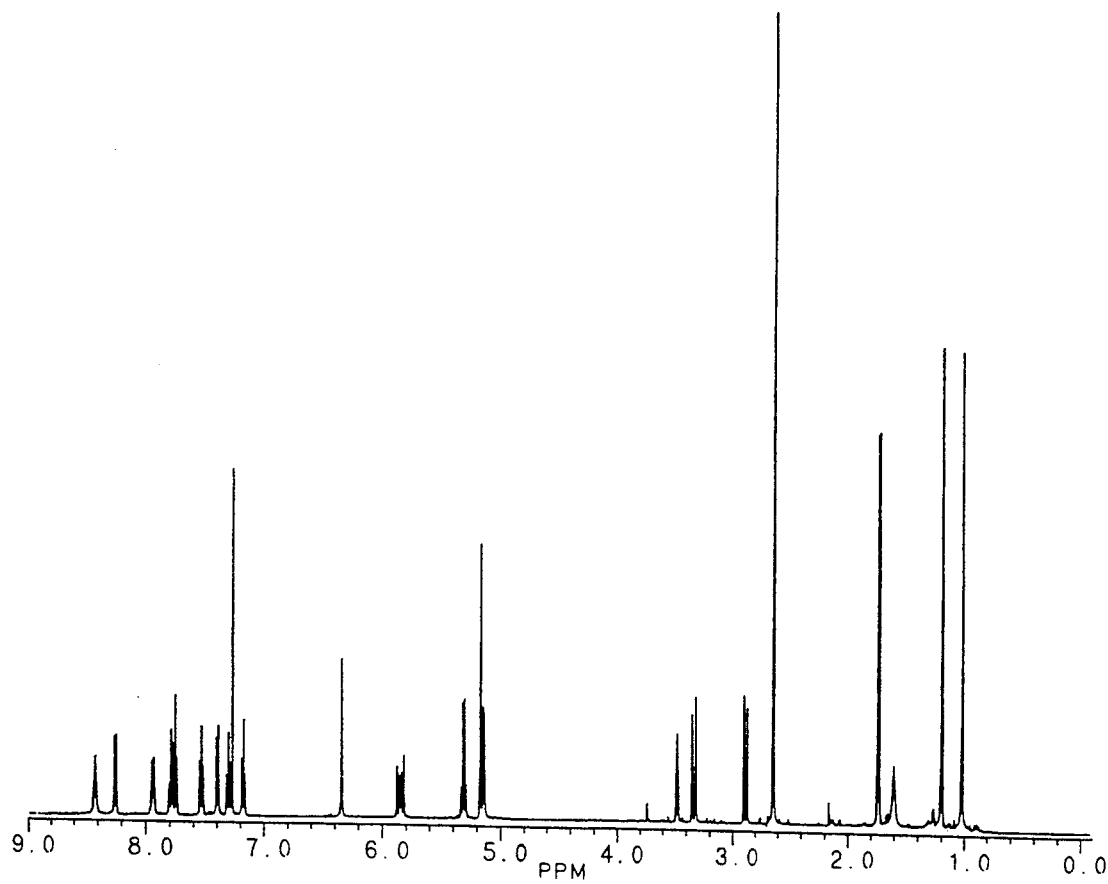
FIG. 13 is an $^1$H NMR spectrum in CDCl$_3$ of 5-N-acetyl-15b-$\alpha$-hydroxyardeemin.
Figure 14:
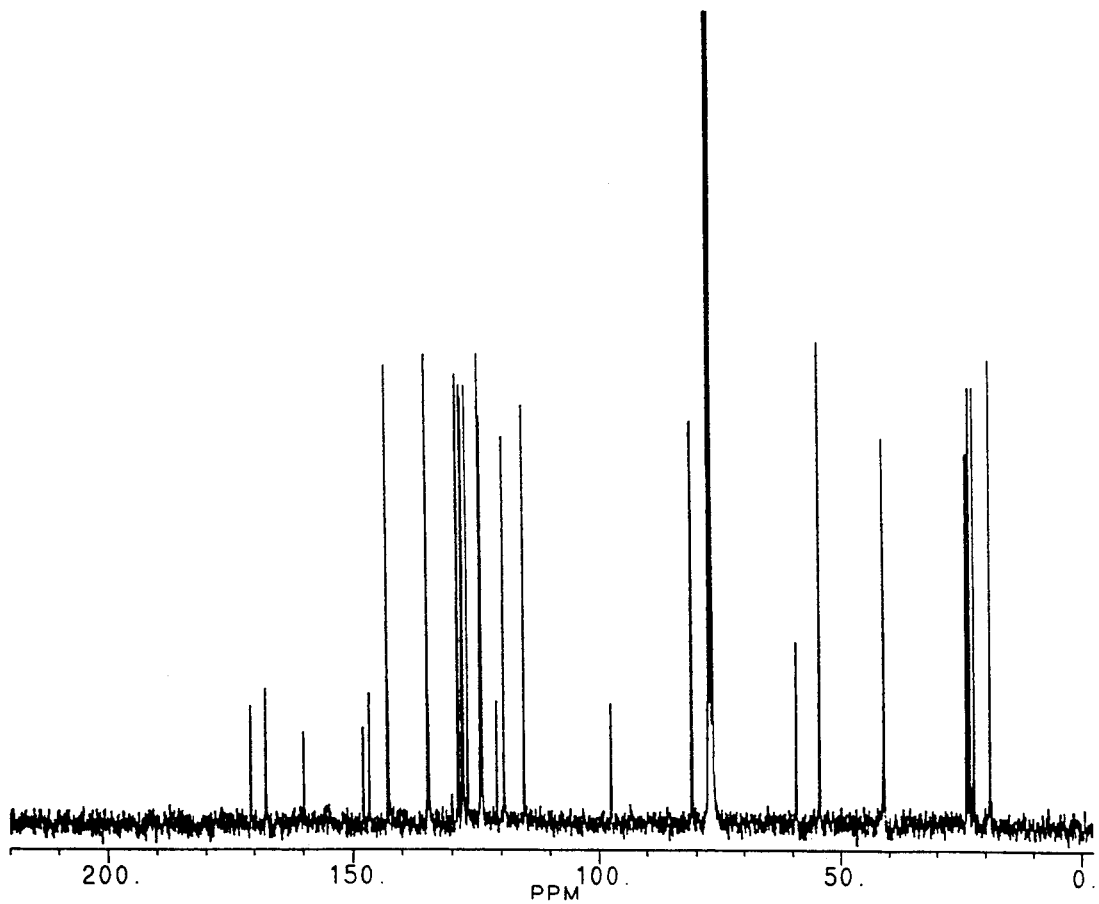
FIG. 14 is a $^{13}$C CMR spectrum in CDCl$_3$ of 5-N-acetyl-15b-$\alpha$-hydroxyardeemin.
Figure 15:
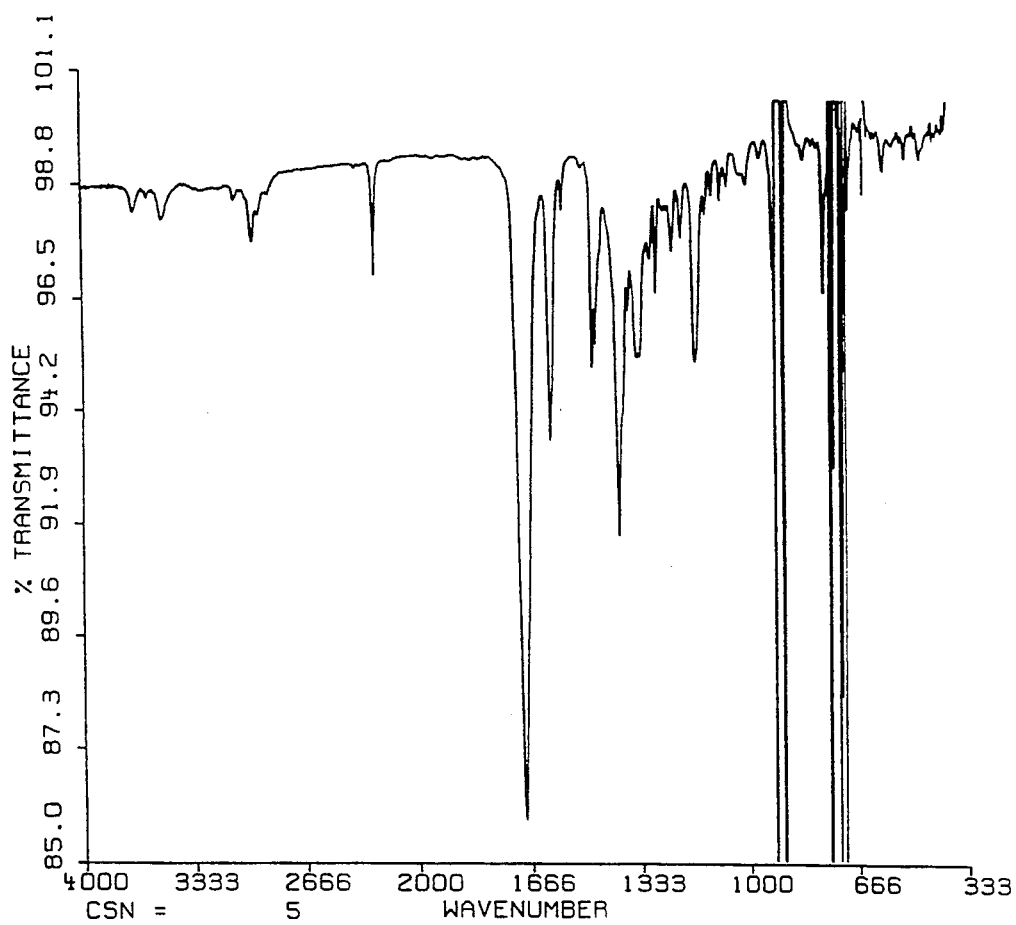
FIG. 15 is an infrared spectrum in CDCl$_3$ of 5-N-acetyl-15b-$\alpha$-hydroxyardeemin.

5-N-Acetyl-15b-$\alpha$-hydroxyardeemin, isolated as pure compound number 5 in Example 3 above, was found to be a white solid, $[\alpha]_D^{25} = -41°$ (c=0.31, MeOH). TLC as described in Example 4 showed the compound to have the following Rf values: Rf=0.66 in EtOAc, Rf=0.50 in CHCl$_3$/MeOH (97/3) and Rf=0.34 in toluene/acetone (2/1). A molecular weight of 484 was established by desorption chemical ionization mass spectroscopy (NH$_3$ gas). An ultraviolet spectrum (MeOH) contained bands at $\lambda_{max}=210$ ($\epsilon=27,000$), 224 ($\epsilon=24,000$), 268 ($\epsilon=9,000$), 274 ($\epsilon=8,500$), 302 ($\epsilon=3,700$), and 314 ($\epsilon=3,000$). These bands were unchanged with the addition of acid or base. $^1$H NMR $^{13}$C NMR, and IR spectra are provided below in FIGS. 13, 14 and 15, respectively.

EXAMPLE 9

15b-$\beta$-Methoxyardeemin (Formula I: $R^1 =$ hydrogen, $R^2 =$ methoxyl)

Figure 16:
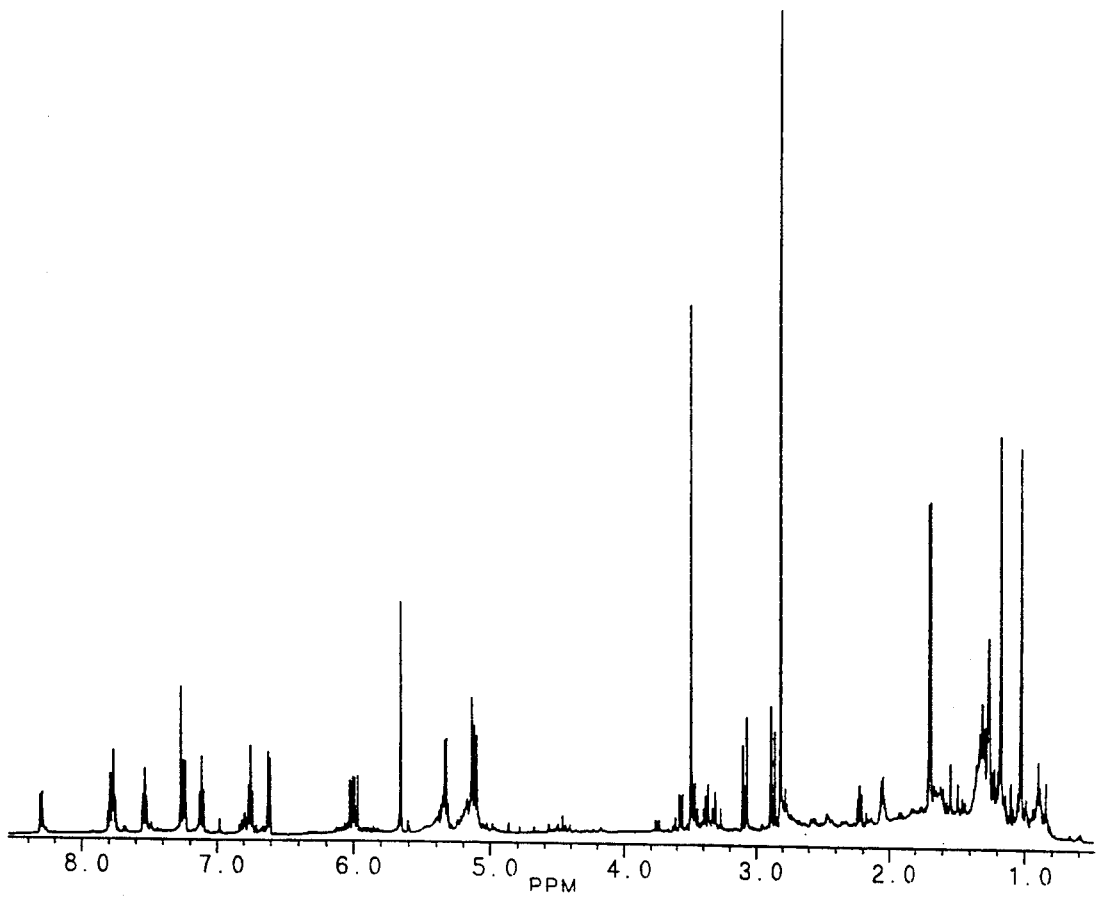
FIG. 16 is an $^1$H NMR spectrum in CDCl$_3$ of 15b-$\beta$-methoxyardeemin.
Figure 17:
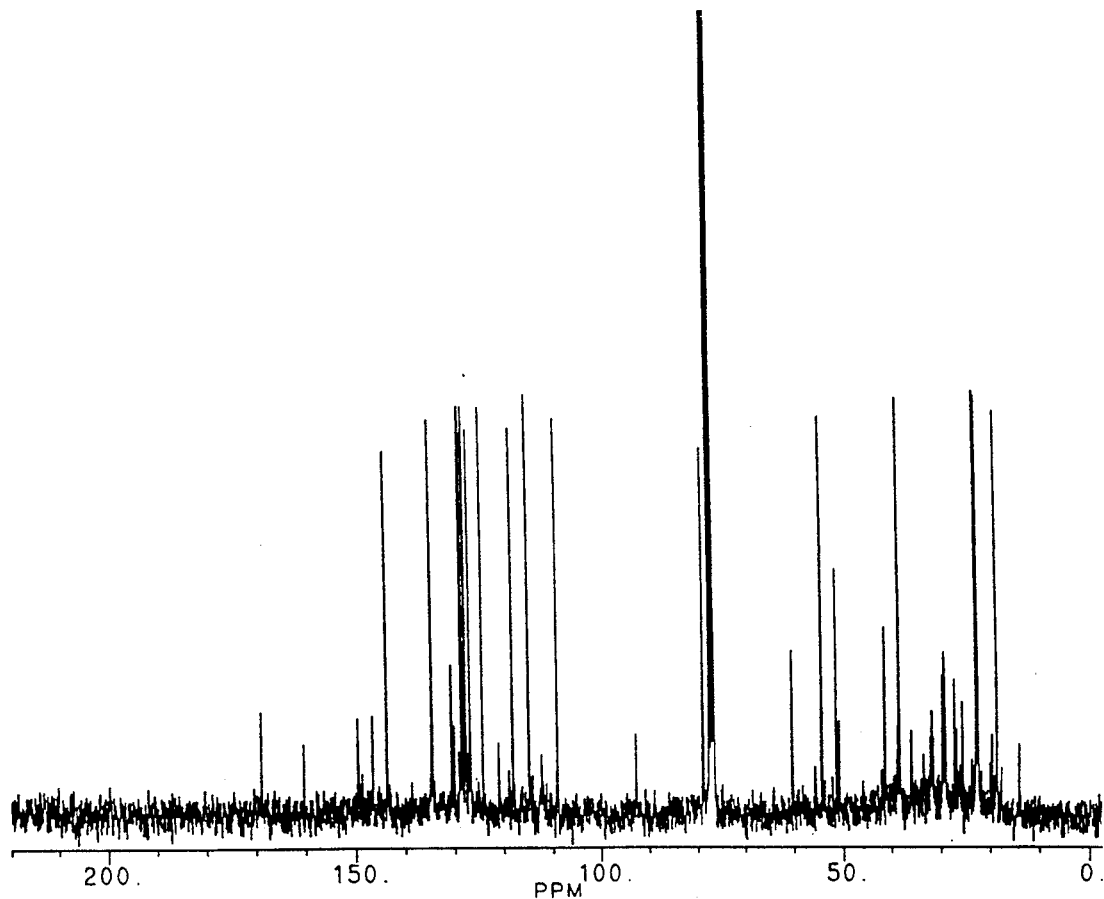
FIG. 17 is a $^{13}$C CMR spectrum in CDCl$_3$ of 15b-$\beta$-methoxyardeemin.
Figure 18:
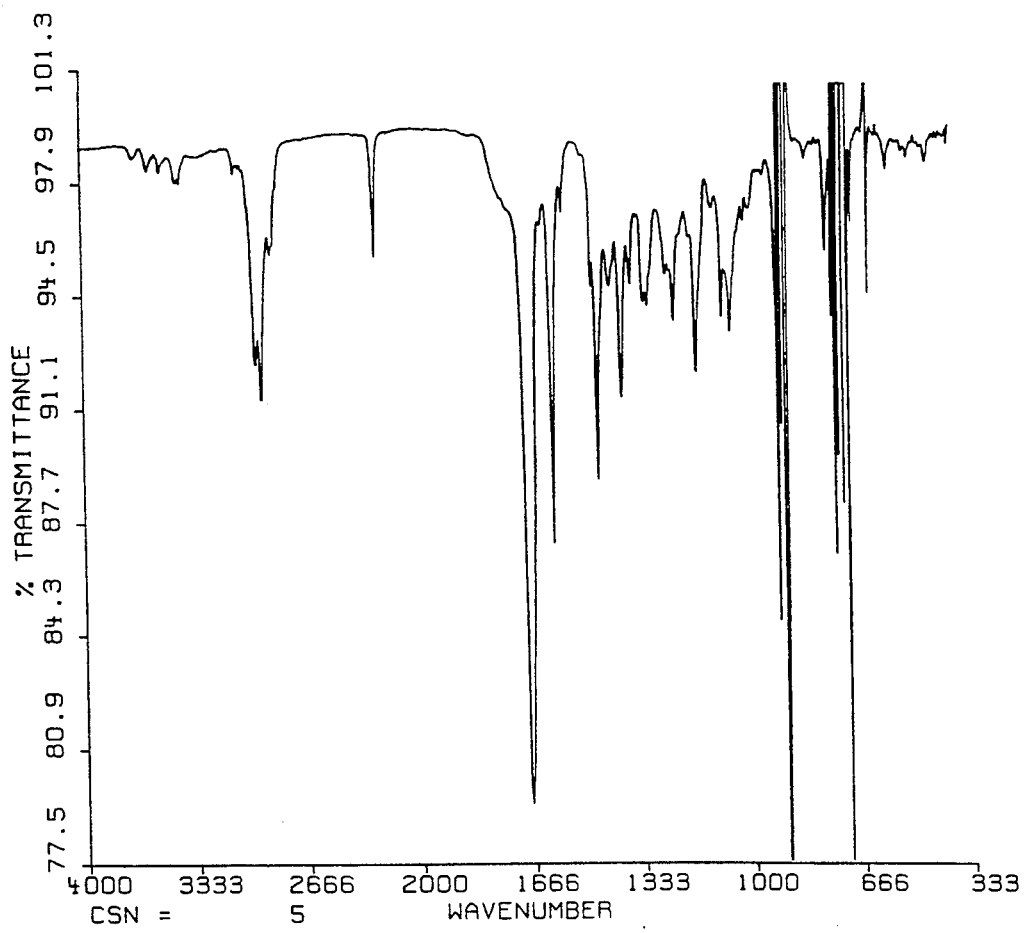
FIG. 18 is an infrared spectrum in CDCl$_3$ of 15b-$\beta$-methoxyardeemin.

15b-$\beta$-Methoxyardeemin, isolated as pure compound number 6 in Example 3 above, was found to be a white solid, $[\alpha]_D^{25} = -169°$ (c=0.63, MeOH). TLC as described in Example 4 showed the compound to have the following Rf values: Rf=0.69 in EtOAc, Rf=0.66 in CHCl$_3$/MeOH (97/3) and Rf=0.64 in toluene/acetone (2/1). A molecular weight of 456 was established by desorption chemical ionization mass spectroscopy (NH$_3$ gas). An ultraviolet spectrum obtained in MeOH contained bands at $\lambda_{max}=210$ ($\epsilon=35,000$), 224 ($\epsilon=20,000$), 268 ($\epsilon=8,500$), 274 ($\epsilon=8,500$), 302 ($\epsilon=5,900$), and 314 ($\epsilon=4,400$). These bands were unchanged with the addition of acid or base. $^1$H NMR $^{13}$C NMR, and IR spectra are provided below in FIGS. 16, 17 and 18, respectively.

EXAMPLE 10

In Vitro Sensitization of Multiple Drug Resistant Cells

The compounds of this invention were tested in an assay to demonstrate chemosensitization of a multiple drug resistant human epidermal cell line. Cytotoxicity assays to determine 50% inhibition of growth (IC$_{50}$) were done in 96-well tissue culture microtiter trays (Costar, Cambridge, Mass.). Cell growth was determined as follows: KB 3-1 (sensitive) and KB V1 (multiple drug resistant) cells grown in Dulbecco's modified Eagle medium (Gibco BRL, Division of Life Technologies, Inc., Grand Island, N.Y.) were added to each microtiter well at $1 \times 10^4$ cells in 200 $\mu$L of growth medium in the presence and absence of verapamil, 5-acetylardeemin and 5-acetyl-15b-$\beta$-hydroxyardeemin at 2.0, 3.3 and 6.6 mM. Anticancer cytotoxic agents adriamycin (ADR), vinblastine (VBL) and vincristine (VCR) (Sigma, St. Louis, Mo.) were added in final concentrations ranging from 0.0001 to 10 $\mu$g/mL. Cells were incubated at 37° C. in a humidified atmosphere of 4% CO$_2$ for 72 hours. Cell growth was measured by the reduction of 3-(4,5-dimethyl-thiazol-2-yl)-2,5-diphenyltetrazolium bromide (MTT), added to each well at 0.1 mg/mL. The plates were incubated at 37° C. in humidified 4% CO$_2$ for 3 hours. The trays were spun at $1000 \times g$ for 10 minutes, the supernatant removed by aspiration and the residual formazan reduction product dissolved in 100 $\mu$L of DMSO. Growth was quantitated by measuring the optical absorbance in each well at 570 nm in a microtiter plate reader. The results, shown in Table 3 as the mean IC$_{50}$ values of triplicate samples, demonstrate the ability of the compounds of the invention to sensitize a MDR cell line to available cytotoxic agents.

TABLE 3

| Chemomodulation of MDR in KB V1 cells | | | | |
|---|---|---|---|---|
| Modulator ($\mu$M) | Cell Type | VBL-IC$_{50}$ ($\mu$g/mL) | VCR-IC$_{50}$ ($\mu$g/mL) | ADR-IC$_{50}$ ($\mu$g/mL) |
| None | KB 3-1 | 0.001 | 0.001 | 0.012 |
| None | KB V1 | 1.2 | 7.0 | 3.0 |
| Verapamil | KB V1 | | | |
| 2.0 | | 0.012 | 0.22 | 0.2 |
| 3.3 | | 0.004 | 0.08 | 0.1 |
| 6.6 | | 0.002 | 0.02 | 0.07 |
| 5-AcA* | KB V1 | | | |
| 2.0 | | 0.02 | 0.4 | 0.3 |
| 3.3 | | 0.004 | 0.08 | 0.1 |
| 6.6 | | 0.001 | 0.001 | 0.04 |
| 5-AcHA** | KB V1 | | | |
| 2.0 | | 0.02 | 0.2 | 0.28 |
| 3.3 | | 0.001 | 0.04 | 0.09 |
| 6.6 | | 0.001 | 0.001 | 0.03 |

*5-N-Acetylardeemin
**5-N-Acetyl-15b-$\beta$-hydroxyardeemin

The above embodiments of the present invention are intended to be illustrative and not restrictive, the scope of the invention being instead defined by the appended claims and equivalencies embraced thereby. It is expected that the particulars of the foregoing description may be readily modified by those skilled in the art without departing from the spirit or essential characteristics thereof.

We claim:

1. A compound having the structural formula

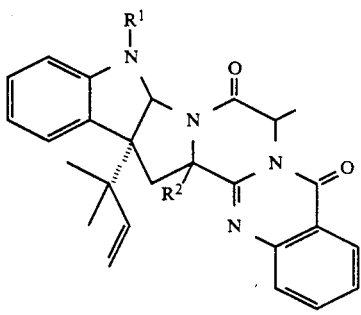

or a pharmaceutically acceptable salts and prodrugs thereof, wherein $R^1$ is selected from the group consisting of hydrogen and loweracyl, and $R^2$ is selected from the group consisting of hydrogen, hydroxyl and methoxyl.

2. A compound according to claim 1, wherein $R^1$ is loweracyl.

3. A compound according to claim 2, wherein $R^2$ is hydroxyl.

4. A compound according to claim 2, wherein $R^1$ is acetyl.

5. A compound according to claim 4, wherein $R^2$ is hydroxyl.

6. A compound selected from the group consisting of:
ardeemin;
5-N-acetylardeemin;
5-N-acetyl-15b-$\beta$-hydroxyardeemin;
15b-$\beta$-hydroxyardeemin;
5-N-acetyl-15b-$\alpha$-hydroxyardeemin; and
15b-$\beta$-methoxyardeemin.

7. A pharmaceutical composition comprising a multiple drug resistance-attenuating amount of a compound according to claim 1 in combination with a pharmaceutically acceptable carrier.

8. A pharmaceutical composition according to claim 7, additionally comprising a therapeutically effective amount of a cytotoxic agent.

9. A pharmaceutical composition comprising a multiple drug resistance-attenuating amount of a compound according to claim 6 in combination with a pharmaceutically acceptable carrier.

10. A pharmaceutical composition according to claim 9, additionally comprising a therapeutically effective amount of a cytotoxic agent.

* * * * *